United States Patent [19]

Mallams et al.

[11] 4,085,208

[45] Apr. 18, 1978

[54] PROCESS FOR PREPARING 4,6-DI-O-(AMINOGLYCOSYL)-1,3-DIAMINOCYCLITOLS AND NOVEL 1-EPIMERS AND 1-N-ALKYL DERIVATIVES PRODUCED THEREBY; METHODS FOR THE USE OF THE 1-EPIMER DERIVATIVES AS ANTIBACTERIAL AGENTS AND COMPOSITIONS USEFUL THEREFOR

[75] Inventors: Alan K. Mallams, West Orange, N.J.; David Huw Davies, Macclesfield, England

[73] Assignee: Schering Corporation, Kenilworth, N.J.

[21] Appl. No.: 697,805

[22] Filed: Jun. 21, 1976

[51] Int. Cl.$^2$ .................. A61K 31/71; C07H 15/22
[52] U.S. Cl. ..................... 424/180; 536/10; 536/17
[58] Field of Search .................. 536/17; 424/180

[56] References Cited

U.S. PATENT DOCUMENTS

| | | | |
|---|---|---|---|
| 3,828,021 | 8/1974 | Beattie et al. | 536/17 |
| 3,868,360 | 2/1975 | Daniels et al. | 536/17 |
| 3,920,628 | 11/1975 | Daniels | 536/17 |
| 4,002,742 | 1/1977 | Wright et al. | 536/17 |

OTHER PUBLICATIONS

Noller, "Chemistry of Organic Compounds", 3rd Ed., W. B. Saunders Co., Phila., Pa., 1965, p. 575.

*Primary Examiner*—Johnnie R. Brown
*Attorney, Agent, or Firm*—Elizabeth A. Bellamy; Mary S. King

[57] ABSTRACT

This invention relates to the preparation of novel 1-epi-aminoglycosides, useful as antibacterial agents, and also relates to the process for the preparation of known as well as novel 1-N-substituted aminoglycoside antibacterial agents.

30 Claims, No Drawings

4,085,208

PROCESS FOR PREPARING 4,6-DI-O-(AMINOGLYCOSYL)-1,3-DIAMINOCYCLITOLS AND NOVEL 1-EPIMERS AND 1-N-ALKYL DERIVATIVES PRODUCED THEREBY; METHODS FOR THE USE OF THE 1-EPIMER DERIVATIVES AS ANTIBACTERIAL AGENTS AND COMPOSITIONS USEFUL THEREFOR

FIELD OF THE INVENTION

This invention relates to novel compositions of matter, to methods for their manufacture and methods for their use as antibacterial agents.

Specifically, this invention relates to novel 1-N-substituted and 1-epi-4,6-di-O-(aminoglycosyl)-1,3-diaminocyclitols useful as antibacterial agents. Further, this invention relates to pharmaceutical compositions comprising said 1-epi-derivatives, to methods for their manufacture, and to methods for their use in treating bacterial infections.

Particularly, this invention relates to novel 1-N-substituted and 1-epi-derivatives of 4-O-(aminoglycosyl)-6-O-garosaminyl-1,3-diaminocyclitol antibiotics including certain gentamicins, sisomicin, verdamicin, Antibiotics G-418, G-52, JI-20A, JI-20B, the 5-epi, 5-epi-azido-5-deoxy, 5-epi-amino-5-deoxy analogs of the foregoing; and Antibiotics Mu-1, Mu-2, Mu-4, and Mu-5.

Moreover, this invention relates to a novel process for the preparation of 4,6-di-O-(aminoglycosyl)-1,3-diaminocyclitols, and novel 1-epimers and novel 1-N-alkyl derivatives.

PRIOR ART

Described in South African Patent No. 74/4939 are 1-N-alkyl-4,6-di-O-(aminoglycosyl)-1,3-diaminocyclitols, in which the carbon adjacent to the aminoglycoside nitrogen in the 1-N-alkyl substituent must be primary.

By out instant invention we have discovered a novel method for preparing the prior art 1-N-alkyl-4,6-di-O-(aminoglycosyl)-1,3-diaminocyclitols. Moreover, our process produces the heretofore unobtainable 1-epimers of the prior art aminoglycosides as well as heretofore unobtainable 1-N-alkyl derivatives wherein the carbon in the alkyl group adjacent to the aminoglycoside nitrogen can be secondary or tertiary — i.e. 1-N-isopropyl, 1-N-tertiary butyl and 1-N-cyclopropyl.

GENERAL DESCRIPTION OF THE INVENTION cl Composition-of-Matter Aspect

The novel composition-of-matter aspect of our invention includes 1-epi-N-X-4,6-di-O-(aminoglycosyl)-1,3-diaminocyclitols selected from the group consisting of 1-epi-N-X-gentamicin A, 1-epi-N-X-gentamicin B, 1-epi-N-X-gentamicin $B_1$, 1-epi-N-X-gentamicin $C_1$, 1-epi-N-X-gentamicin $C_{1a}$, 1-epi-N-X-gentamicin $C_2$, 1-epi-N-X-gentamicin $C_{2a}$, 1-epi-N-X-gentamicin $C_{2b}$, 1-epi-N-X-gentamicin $X_2$, 1-epi-N-X-kanamycin A, 1-epi-N-X-kanamycin B, 1-epi-N-X-3′, 4′-dideoxykanamycin B, 1-epi-N-X-sisomicin, 1-epi-N-X-verdamicin, 1-epi-N-X-tobramycin, 1-epi-N-X-Antibiotics G-52, G-418, 66-40B, 66-40D, JI-20A, JI-20B, the 5-epi, 5-epi-azido-5-deoxy, 5-epi-amino-5-deoxy analogs of the foregoing; and 1-epi-N-X-Mu-1, Mu-2, Mu-4, Mu-5 and the pharmaceutically acceptable acid addition salts thereof. In the foregoing 1-epi-N-X-derivatives, X is a substituent selected from the group consisting of hydrogen, alkyl, alkenyl, cycloalkyl, cycloalkylalkyl, aralkyl, hydroxyalkyl, aminoalkyl, alkylaminoalkyl, dialkylaminoalkyl, aminohydroxyalkyl, alkylaminohydroxyalkyl and dialkylaminohydroxyalkyl, said X substituent having less than 9 carbon atoms with the proviso that said aminohydroxyalkyl, alkylaminohydroxyalkyl, and dialkylaminohydroxyalkyl substituents must have the amino and hydroxyl groups on different carbon atoms, and that neither substituent be on the carbon atom α- to the 1-amino function.

Included among the substituents contemplated for the moiety X in our novel compounds are hydrogen, straight and branched chain alkyl groups such as ethyl, n-propyl, isopropyl, n-butyl, isobutyl, tertiary-butyl, β-methylpropyl, n-pentyl, isopentyl, β-methylbutyl, γ-methylbutyl and β,β-dimethylpropyl: n-hexyl, δ-methylpentyl, β-ethylbutyl, γ-ethylbutyl, n-heptyl, iso-heptyl, ε-methylheptyl, β-ethylpentyl, γ-ethylpentyl, δ-ethylpentyl, γ-propylbutyl, n-octyl, iso-octyl, β-ethylhexyl, δ-ethylhexyl, ε-ethylhexyl, β-propylpentyl, γ-propylpentyl; alkenyl groups such as β-propenyl, β-methylpropenyl, β-butenyl, β-methyl-β-butenyl and β-ethyl-β-hexenyl; cycloalkyl groups such as cyclopropyl, cyclobutyl, cyclopentyl and cyclohexyl; cycloalkylalkyl groups such as cyclopropylmethyl, cyclobutylmethyl, cyclopentylmethyl and cyclohexylmethyl; aralkyl groups such as benzyl, o-tolyl, m-tolyl, p-tolyl and phenylethyl; hydroxy substituted straight and branched chain alkyl groups such as ε-hydroxypentyl, β-hydroxy-γ-methylbutyl, β-hydroxy-β-methylpropyl, δ-hydroxybutyl, β-hydroxypropyl, γ-hydroxypropyl, β-hydroxyethyl, ω-hyroxyoctyl; amino substituted straight and branched chain alkyl groups such as ε-aminopentyl, β-aminopropyl, γ-aminopropyl, δ-aminobutyl, β-amino-γ-methylbutyl and ω-aminooctyl; and mono-N- and poly-N-alkylated derivatives thereof such as the N-methyl, N,N-dimethyl, N-ethyl, N,N-diethyl, N-propyl and N,N-dipropyl, e.g. ε-methylaminopentyl, ε-dimethylaminopentyl, β-methylaminopropyl, γ-methylaminopropyl, β-dimethylaminopropyl, γ-dimethylaminopropyl, β-ethylaminopropyl, β-diethylaminopropyl, ε-methylaminobutyl, δ-dimethylaminobutyl, β-methylamino-γ-methylbutyl, and ω-methylaminobutyl; aminopropyl, δ-methylaminobutyl, β-methylamino-γ-methylbutyl, and ω-methylaminobutyl, amino and hydroxy disubstituted straight and branched chain alkyl groups such as β-hydroxy-ε-aminopentyl, γ-hydroxy-γ-methyl-δaminobutyl, β-hydroxy-δ-aminobutyl, β-hydroxy-γ-aminopropyl, and β-hydroxy-β-methyl-γ-aminopropyl; and mono-N- and poly-N-alkylated derivatives thereof such as β-hydroxy-ε-methylaminopentyl, γ-hydroxy-γ-methyl-δ-methylaminobutyl, β-hydroxy-δ-methylaminobutyl, β-hydroxy-δ-dimethylaminobutyl, β-hydroxy-γ-ethylaminopropyl, β-hydroxy-β-methyl-γ-methylaminopropyl and β-hydroxy-γ-dimethylaminopropyl.

Of the foregoing substituents contemplated for the moiety "X", preferred are those wherein X is hydrogen or contains 2–4 carbon atoms.

The preferred 1-epi-N-X-4,6-di-O-(aminoglycosyl)-1,3-diaminocyclitols of this invention are those wherein the 6-O-aminoglycosyl unit is 6-O-garosaminyl, including the 1-epi-N-X-derivatives of gentamicins B, $B_1$, $C_1$, $C_{1a}$, $C_2$, $C_{2a}$, $C_{2b}$, $X_2$, sisomicin, verdamicin, Antibiotics G-52, G-418, JI-20A, JI-20B, the 5-epi, 5-epi-azido-5-deoxy, 5-epi-amino-5-deoxy analogs of the foregoing; and Antibiotics Mu-1, Mu-2, Mu-4, and Mu-5. Of the foregoing, particularly preferred are those wherein the 1,3-diaminocyclitol is 2-deoxystreptamine, i.e. 1-epi-N-X-derivatives of 4-O-(aminoglycosyl)-6-O-garosaminyl-2-deoxystreptamines such as gentamicins B, $B_1$, $C_1$, $C_{1a}$, $C_2$, $C_{2a}$, Chd 2b, $X_2$, sisomicin, verdamicin and Antibiotics G-52, G-418, JI-20A and JI-20B. Particularly valuable derivatives of the foregoing are 1-episisomicin, 1-epi-N-ethylsisomicin, 1-epi-N-($\gamma$-dimethylaminopropyl)-sisomicin, 1-epi-N-isopropylgentamicin $C_1$ and 1-epi-N-($\beta$-hydroxyethyl) gentamicin $C_1$.

Also included within this composition-of-matter aspect of this invention are the pharmaceutically acceptable acid addition salts of the 1-epi-N-X-4,6-di-O-(aminoglycosyl)-1,3-diaminocyclitols described hereinabove, which are made according to known procedures such as by neutralizing the free base with the appropriate acid usually to about pH 5. Included among the pharmaceutically acceptable acid addition salts of this invention are those derived from organic acids such as acetic acid, propionic acid, succinic acid, fumaric acid and maleic acid, or, preferably, from inorganic acids such as hydrochloric, sulfuric, phosphoric and hydrobromic. The physical embodiments of the acid addition salts of this invention are characterized by being white solids which are soluble in water, sparingly soluble in most polar organic solvents and insoluble in most nonpolar organic solvents.

In general, the microbiological activity of the 1-epi-N-X-4,6-di-O-(aminoglycosyl)-1,3-diaminocyclitols of this invention and their pharmaceutically acceptable acid addition salts, is similar to that of the corresponding normal 1-N-X-derivatives of 4,6-di-O-(aminoglycosyl)-1,3-diaminocyclitols, both in vitro and in vivo, but advantageously they are less acutely toxic than the normal 1-N-X-derivatives. The 1-epi-N-X-aminoglycosides are broad spectrum antibacterials active against both gram-negative and gram-positive strains, being particularly active against pathogenic types of gram-negative bacteria such as E. coli and Pseudomonas and gram-positive bacteria such as Staphylococcus.

Still another composition-of-matter aspect of this invention are 1-N-X-4,6-di-O-(aminoglycosyl)-1,3-diaminocyclitols wherein X is a carbon-containing substituent in which the carbon of said substituent X, adjacent to the nitrogen of the aminoglycoside is either secondary or tertiary. Exemplary derivatives of this aspect of our invention are 1-N-isopropyl, 1-N-isobutyl, 1-N-tertiary butyl, 1-N-cyclopropyl, and 1-N-cyclobutyl derivatives of 4,6-di-O-(aminoglycosyl)-1,3-diaminocyclitols, such as those described hereinabove in connection with the 1-epi-N-substituted derivatives of this invention. These novel 1-N-alkyl-aminoglycosides were not available prior to our invention since as discussed hereinabove, the prior art teaches only the preparation of 1-N-alkylaminoglycosides in which the carbon atom adjacent to the 1-N-aminoglycoside must be unsubstituted.

As in the 1-epi-N-X-4,6-di-O-(aminoglycosyl)-1,3-diaminocyclitol aspect of this invention, the particularly preferred compounds are those wherein the 6-O-aminglycosyl unit is 6-O-garosaminyl and the 1,3-diaminocyclitol unit is 2-deoxystreptamine. Thus are included the 1-N-X-derivatives of 4-O-aminoglycosyl-6-O-garosaminyl-2-deoxystreptamines such as gentamicins B, $B_1$, $C_1$, $C_{1a}$, $C_2$, $C_{2a}$, $C_{2b}$, $X_2$, sisomicin, verdamicin, and Antibiotics G-52, G-418, JI-20A, and JI-20B. Particularly valuable derivatives of the foregoing are 1-N-isopropylsisomicin and 1-N-isopropylgentamicin $C_1$.

Also included within the composition-of-matter aspect of this invention are the pharmaceutically acceptable acid addition salts of the 1-N-alkyl-4,6-di-O-(aminoglycosyl)-1,3-diaminocyclitols described hereinabove, which are made according to the same methods as described in connection with the 1-epi-N-X-4,6-di-O-(aminoglycosyl)-1,3-diaminocyclitol aspect of this invention.

In general the microbiological activity of the 1-N-alkylaminoglycosides of this invention as described hereinabove and their pharmaceutically acceptable acid addition salts is similar to that of the parent compounds both in vitro and in vivo, but generally they are less acutely toxic than their precursor aminoglycosides and are active against many strains of bacteria that are resistant to the parent aminoglycosides.

Process Aspect of the Invention

The invention sought to be patented in its process aspect is the preparation of 1-N-X-and 1-epi-N-X-derivatives of a 4,6-di-O-(aminoglycosyl)-1,3-diaminocyclitol wherein X is a substituent selected from the group consisting of hydrogen, alkyl, alkenyl, cycloalkyl, cycloalkylalkyl, aralkyl, hydroxyalkyl, aminoalkyl, alkylaminoalkyl, dialkylaminoalkyl, aminohydroxyalkyl, alkylaminohydroxyalkyl and dialkylaminohydroxyalkyl, said X substituent having less than 9 carbon atoms with the proviso that said aminohydroxyalkyl, alkylaminohydroxyalkyl and dialkylaminohyroxyalkyl substituents must have the amino and hydroxy groups on different carbon atoms and that neither substituent be on the $\alpha$-carbon atom.

The process comprises the reaction of a 1-desamino-1-oxo-4,6-di-O-(aminoglycosyl)-1,3-diaminocyclitol, having all primary amines protected (synonomous with "blocked") with an amino protecting group, in an inert solvent in the pH range of about 5–14 with at least a molar equivalent of a primary amine having the formula X—$NH_2$ wherein X is as previously defined, thence with at least one equivalent of an appropriate hydride donor reducing agent followed by the removal of the N-protecting groups. Thus, there is produced a product mixture comprising the 1-N-X-4,6-di-O-(aminoglycosyl)-1,3-diaminocyclitol and the 1-epi-N-X-4,6-di-O-(aminoglycosyl)-1,3-diaminocyclitol which is separated, usually utilizing chromatographic techniques, to produce the 1-N-X-and the 1-epi-N-X-derivatives of this invention.

The 1-desamino-1-oxo-poly-N-protected-4,6-di-O-(aminoglycosyl)-1,3-diaminocyclitols, starting compounds of this invention are the subject of our co-pending application, Ser. No. 697,804 filed June 21, 1976, 1-DESAMINO-1-HYDROXY AND 1-DESAMINO-1-EPI-HYDROXY-4,6-DI-O-(AMINOGLYCOSYL)-1,3-DIAMINOCYCLITOLS, METHODS FOR THEIR MANUFACTURE AND NOVEL 1-DESAMINO-1-OXO-4,6-DI-O-(AMINO-GLYCOSYL)-1,3-DIAMINOCYCLITOLS, INTERMEDIATES USEFUL THEREIN, METHODS FOR THEIR USE AS ANTIBACTERIAL AGENTS AND COMPOSITIONS USEFUL THEREFOR. In brief, the 1-desamino-1-oxo-poly-N-protected aminoglycosides are prepared by treating an aminoglycoside having all primary amines protected other than at position 1 with a mild oxidizing agent such as 3,5-di-tert.-butyl-1,2-benzoquinone. The 1-imine derivative thus formed by prototropic shift is reacted with acid to form the requisite 1-desamino-1-oxo-poly-N-protected aminoglycoside.

When carrying out the process of this invention, the 1-desamino-1-oxo starting compounds are "blocked" or "protected" at any primary amino groups, although secondary amino groups may also be protected. The terms "blocking" groups and "protecting" groups are used synonomously and each are art recognized terms as being amino derivatives which temporarily block, or protect, an amino function in the aminoglycoside molecule from undergoing chemical reactions, yet which are readily removable after a desired chemical reaction is effected at another site on the molecule.

Amino protecting groups which are useful in our process include acetyl, trifluoroacetyl, benzoyl, trichloroethoxycarbonyl, benzyloxycarbonyl and ethoxycarbonyl. The choice of protecting groups used in our starting compounds is governed by the desired solubility characteristics and stability of the intermediate blocked derivatives. The above, as well as the choice of the reaction conditions and the method desired for removing, or deblocking said groups, is within the knowledge of one skilled in the aminoglycoside art.

As discussed hereinabove, in carrying out our process, it is necessary only to "block", or "protect" any primary amino groups in the aminoglycoside molecule, however, in some cases in order to increase the stability of the 1-desamino-1-oxo-derivatives of the blocked aminoglycosides, it may be desirable to also protect any secondary amino groups in the molecule. For example, gentamicin $C_{1a}$ can be protected not only at the 3,2' and 6'-positions, but also at the 3''-position. In one mode of carrying out our process (as illustrated in the Preparations) a trichloroethoxycarbonyl group is used to block the 3,2' and 6'-primary amino groups and an acetyl group is used to block the secondary amino group at the 3''-position. Alternatively, tetra-N-acetyl derivative could also be used in our process. It is also possible to protect secondary amino groups by virtue of the blocking procedure used. For example, in the acetylation method of Preparation 2B, Antibiotic G-52 will automatically be acetylated at the secondary amino group at position-6'. However, this blocking at 6'- is not necessary for carrying out the process for the further utilization of Antibiotic G-52.

In carrying out the process of our invention, the 1-desamino-1-oxo-poly-N-protected-4,6-di-O-(aminoglycosyl)-1,3-diaminocyclitol is reacted at ambient temperatures in an inert solvent in the pH range of about 5–14 with at least a molar equivalent of a primary amine having the formula X—$NH_2$. The imine thus formed in situ is reacted with at least one equivalent of a hydride donor reducing agent. The amino protecting groups in the resultant reduced product may then be deblocked utilizing conventional techniques to produce a mixture of the 1-N-X-4,6-di-O-(aminoglycosyl)-1,3-diaminocyclitol and the 1-epi-N-X-4,6di-O-(aminoglycosyl)-1,3-diaminocyclitol. Utilizing chromatographic techniques, the foregoing mixture is then separated into its component parts, i.e. the 1-N-X-aminoglycoside and the 1-epi-N-X-aminoglycoside.

Inert solvents suitable for our process are lower alkanols such as methanol, ethanol and propanol; dioxane and tetrahydrofuran. The solvent utilized should be compatible with the solubility and stability of the N-blocked aminoglycosides and the hydride donor reducing agents, which are known to those skilled in the art.

For example, if acetyl, or trifluoroacetyl are used as blocking groups, the solvent system is preferably methanol; whereas, when using benzoyl, or trichloroethoxycarbonyl blocking groups, a solvent such as tetrahydrofuran is utilized.

The choice of hydride-donor reducing agents utilized in our process is dependent upon the particular starting aminoglycoside. For example, those aminoglycosides which contain unsaturation, e.g. sisomicin, verdamicin, Antibiotics G-52, 66-40B, 66-40D, Mu-1, Mu-2, Mu-4, Mu-5, require the use of a reducing agent which will not destroy the double bond, e.g. sodium cyanoborohydride, sodium borohydride, morpholinoborane, N,N-diethylanilinoborane, and stereoselective trialkylborohydrides such as K-selectride ® and L-selectride ®. Aminoglycoside starting compounds of our process devoid of unsaturations may be reduced with any of the above reagents as well as with diborane and the stereoselective trialkylborohydride, 9-BBN ®.

The solvents used in this reduction and the pH of the reaction mixture will be dependent on the solubility and stability of the 1-desamino-1-oxo-poly-N-blocked aminoglycoside and the particular hydride-donor reducing agent being employed. For example, when utilizing an acetyl blocked aminoglycoside and sodium cyanoborohydride, the reaction is carried out in methanol at about pH 5; when utilizing a benzoyl blocked aminoglycoside and K-selectride ® as reducing agent the reaction is carried out in tetrahydrofuran at a pH about 14.

The invention described hereinabove is illustrated in detail hereinbelow in the Preparations and Examples which should not be construed as limiting the scope of our invention.

PREPARATIONS

1-Desamino-1-Oxo-Poly-N-Protected-4,6-Di-O-(Aminoglycosyl)-1,3-Diaminocyclitols

PREPARATION 1

A.

1-Desamino-1-oxo-3,2'-Di-N-trifluoroacetylgentamicin $C_1$

To a solution of 3.34 gm. of 3,2'-di-N-trifluoroacetylgentamicin $C_1$ in 60 ml. anhydrous methanol add 1.12 gm. 3,5-di-t-butyl-1,2-benzoquinone. Stir the solution at 25° C under dry nitrogen for 24 hours. Acidify the solution to pH 2.5 to 3.0 with 2N sulfuric acid and continue stirring at 25° C. Follow the hydrolysis by thin layer chromatography, when complete (after about 4 hours), dilute the mixture with water and filter the solids. Extract the aqueous phase with chloroform (2 × 200 ml.) and adjust pH to 6 with Amberlite IRA 401S(OH—) resin. Filter the resin and evaporate the filtrate in vacuo to obtain 1-desamino-1-oxo-3,2'-di-N-trifluoroacetylgentamicin $C_1$ as the sulfate salt, $[\alpha]_D^{26}$ + 129.5° ($H_2O$); ν max (KBr) 3200, 1680, 1540, 1100 $cm^{-1}$; δ ($D_2O$) 1.21 (3H,d,J7Hz,6'—$CH_3$), 1.28 (3H,s,4''—$CH_3$), 2.69 (3H,s,6'—$NCH_3$) and 2.89 ppm. (3H,s,3''—$NCH_3$).

B.

1-Desamino-1-oxo-poly-N-trifluoroacetyl-4,6-di-O-(aminoglycosyl)-1,3-diaminocyclitols In a manner similar to Preparation 1A, treat the following compounds with 3,5-di-t-butyl-1,2-benzoquinone in acid media:

3,2'-di-N-trifluoroacetylgentamicin A,
3,6'-di-N-trifluoroacetylgentamicin B,
3,6'-di-N-trifluoroacetylgentamicin $B_1$,
3,2'-di-N-trifluoroacetylgentamicin $C_2b$,
3,2'-di-N-trifluoroacetylgentamicin $X_2$,
3,2'-di-N-trifluoroacetyl Antibiotic G-418,
3,2',6'-tri-N-trifluoroacetyl Antibiotic JI-20A,
3,2',6'-tri-N-trifluoroacetyl Antibiotic JI-20B,
3,2',6',3''-tetra-N-trifluoroacetylkanamycin B, and the 5-epi, 5-epi-azido-5-deoxy, 5-epi-amino-5-deoxy analogs of the foregoing and of 3,2'-di-N-trifluoroacetylgentamicin $C_1$. Isolate and purify each of the resultant products to obtain respectively:

1-desamino-1-oxo-3,2'-di-N-trifluoroacetylgentamicin A,
1-desamino-1-oxo-3,6'-di-N-trifluoroacetylgentamicin B,
1-desamino-1-oxo-3,6'-di-N-trifluoroacetylgentamicin $B_1$,
1-desamino-1-oxo-3,2'-di-N-trifluoroacetylgentamicin $C_2b$,
1-desamino-1-oxo-3,2'-di-N-trifluoroacetylgentamicin $X_2$,
1-desamino-1-oxo-3,2'-di-N-trifluoroacetyl Antibiotic G-418, 1-desamino-1-oxo-3,2',6'-tri-N-trifluoroacetyl Antibiotic JI-20A,
1-desamino-1-oxo-3,2',6'-tri-N-trifluoroacetyl Antibiotic JI-20B,
1-desamino-1-oxo-3,2',6',3''-tetra-N-trifluoroacetylkanamycin B, and the 5-epi, 5-epi-azido-5-deoxy, 5-epi-amino-5-deoxy analogs of the foregoing and of 1-desamino-1-oxo-3,2'-di-N-trifluoroacetylgentamicin $C_1$.

PREPARATION 2

A. 1-Desamino-1-oxo-3,2',6'-tri-N-acetylsisomicin

Dissolve 5 gm. of 3,2',6'-tri-N-acetylsisomicin in 200 ml. anhydrous methanol. To this solution add 1.92 gm. 3,5-di-t-butyl-1,2-benzoquinone and stir under dry nitrogen at 25° C for 25 hours. With 2N sulfuric acid acidify the solution to pH 3, stir the mixture at 25° C and follow the hydrolysis by thin layer chromatography. The reaction will be complete after about 15 hours. Dilute the mixture with water and then extract with 3 × 50 ml. chloroform. Neutralize the aqueous layer to pH 7 with 2N ammonium hydroxide and then pass over Amberlite 1R 45 resin. Concentrate the aqueous eluate in vacuo and lyophilize to obtain 1-desamino-1-oxo-3,2',6'-tri-N-acetylsisomicin, $[\alpha]_D^{26}$ + 186.1° (H$_2$O); $\nu$ max (KCl) 3200, 1020 cm$^{-1}$; $\delta$ (D$_2$O) 1.30 (3H, s, 4''—CH$_3$), 1.87, 1.91, 1.96 (9H, s, NHAc) and 2.90 ppm. (3H, s, 3''—NCH$_3$).

B.
1-Desamino-1-oxo-poly-N-acetyl-4,6-di-O-(aminoglycosyl)-1,3-diaminocyclitols In a manner similar to Preparation 2A, treat the following compounds with 3,5-di-t-butyl-1,2-benzoquinone in acid media:

3,2',6'-tri-N-acetylverdamicin,
3,2',6'-tri-N-acetyl Antibiotic G-52,
3,2',6'-tri-N-acetyl Antibiotic 66-40B,
3,2',6'-tri-N-acetyl Antibiotic 66-40D, the 5-epi, 5-epi-azido-5-deoxy, 5-epi-amino-5-deoxy analogs of the foregoing and of 3,2',6'-tri-N-acetylsisomicin; and
3,2',6'-tri-N-acetyl Antibiotic Mu-1,
3,2',6'-tri-N-acetyl Antibiotic Mu-2,
3,2',6'-tri-N-acetyl Antibiotic Mu-4 and
3,5,2',6'-tetra-N-acetyl Antibiotic Mu-5.

Isolate and purify each of the resultant products to obtain respectively:

1-desamino-1-oxo-3,2',6'-tri-N-acetylverdamicin,
1-desamino-1-oxo-3,2',6'-tri-N-acetyl Antibiotic G-52,
1-desamino-1-oxo-3,2',6'-tri-N-acetyl Antibiotic 66-40B,
1-desamino-1-oxo-3,2',6'-tri-N-acetyl Antibiotic 66-40D,
the 5-epi, 5-epi-azido-5-deoxy, 5-epi-amino-5-deoxy analogs of the foregoing and of 1-desamino-1-oxo-3,2',6'-tri-N-acetylsisomicin; and 1-desamino-1-oxo-3,2',6'-tri-N-acetyl Antibiotic Mu-1,
1-Desamino-1-oxo-3,2',6'-tri-N-acetyl Antibiotic Mu-2,
1-desamino-1-oxo-3,2',6'-tri-N-acetyl Antibiotic Mu-4, and
1-desamino-1-oxo-3,5,2',6'-tetra-N-acetyl Antibiotic Mu-5.

PREPARATION 3

A.
1-Desamino-1-oxo-3,2',6'-tri-N-(2,2,2-trichloroethoxycarbonyl) gentamicin $C_{1a}$ Dissolve 3.5 gms. 3,2',6'-tri-N-(2,2,2-trichloroethoxycarbonyl) gentamicin $C_{1a}$ in 70 ml. anhydrous methanol. To the solution add 770 mg. 3, 5-di-t-butyl-1,2-benzoquinone and stir at 25° C for 7 hours under nitrogen. Acidify the solution to pH 3 with sulfuric acid and stir the mixture at 25° C for 17 hours. Neutralize the solution to pH 7 with Amberlite IR 45 resin, filter and evaporate the filtrate to dryness. Chromatograph the residue on a silica gel column (20 × 3.5 cm) by gradient elution using chloroform (1.5 L), 1% methanol in chloroform (1 L) and 5% methanol in chloroform (1 L) as the eluant. Evaporate the fractions of the 5% methanol in chloroform eluant to obtain 1-desamino-1-oxo-3,2',6'-tri-N-(2,2,2-trichloroethoxycarbonyl) gentamicin $C_{1a}$, $[\alpha]_D^{26}$ + 86.4° (CHCl$_3$); $\nu$ max (KBr) 3425, 3350, 1720, 1520, 1100, 1040 cm.$^{-1}$.

B.
1-Desamino-1-oxo-poly-N-(2,2,2-trichloroethoxycarbonyl)-4,6-di-O-(aminoglycosyl)-1,3-diaminocyclitols:

In a manner similar to Preparation 3A, treat the following compounds with 3,5-di-t-butyl-1,2-benzoquinone:

3,2',6'-tri-N-(2,2,2-trichloroethoxycarbonyl) gentamicin $C_2$, 3,2',6'-tri-N-(2,2,2-trichloroethoxycarbonyl) gentamicin $C_{2a}$, and the 5-epi, 5-epi-azido-5-deoxy, 5-epi-amino-5-deoxy analogs of the foregoing and of 3,2',6'-tri-N-(2,2,2-trichloroethoxycarbonyl) gentamicin $C_{1a}$. Isolate each of the resultant products to obtain respectively:

1-desamino-1-oxo-3,2',6'-tri-N-(2,2,2-trichloroethoxycarbonyl) gentamicin $C_2$,
1-desamino-1-oxo-3,2',6'-tri-N-(2,2,2-trichloroethoxycarbonyl) gentamicin $C_{2a}$, and the 5-epi, 5-epi-azido-5-deoxy, 5-epi-amino-5-deoxy analogs of the foregoing and of 1-desamino-1-oxo-3,2',6'-tri-N-(2,2,2-trichloroethoxycarbonyl) gentamicin $C_{1a}$.

PREPARATION 4

A.
1-Desamino-1-oxo-3,2',6'-tri-N-(2,2,2-trichloroethoxycarbonyl)-3''-N-acetylgentamicin $C_{1a}$ Dissolve 1 gm. 3,2',6'-tri-N-(2,2,2-trichloroethoxycarbonyl)-3''-N-acetyl gentamicin $C_{1a}$ in 30 ml. anhydrous methanol. To the solution add 216 mg. 3,5-di-t-butyl-1,2-benzoquinone and stir at 25° C for about 7 hours under nitrogen. Acidify the solution to pH 3 with sulfuric acid and stir the mixture at 25° C for 17 hours. Neutralize the solution to pH 7 with Amberlite IR 45 resin, filter and evaporate the filtrate to dryness. Chromatograph the residue on a silica gel column (20 × 1.5 cm) by gradient elution using chloroform (1.5 L.), 1% methanol in chloroform (1 L.) followed by 5% methanol in chloroform (1 L.) as the eluant. Evaporate the fractions of the 5% methanol in chloroform eluant to obtain 1-desamino-1-oxo-3,2',6'-tri-N-(2,2,2-trichloroethoxycarbonyl)-3''-N-acetyl gentamicin $C_{1a}$.

B.
1-Desamino-1-oxo-poly-N-protected-4,6-di-O-(aminoglycosyl)-1,3-diaminocyclitols In a manner similar to Preparation 4A, treat the following compounds with 3,5-di-t-butyl-1,2-benzoquinone.

3,2',6',-3''-tetra-N-acetyl-3',4'-dideoxykanamycin B,
3,2',6',3''-tetra-N-acetyltobramycin,
3,6',3''-tri-N-acetylkanamycin A, the 5 epi, 5-epi-azido-5-deoxy, 5-epi-amino-5-deoxy analogs of the foregoing and of 3,2',6'-tri-N-(2,2,2-trichloroethoxycarbonyl)-3''-N-acetyl gentamicin $C_{1a}$. Isolate each of the resultant products to obtain respectively:

1-desamino-1-oxo-3,2',6',3''-tetra-N-acetyl-3',4'-dideoxykanamycin B,
1-desamino-1-oxo-3,2',6',3''-tetra-N-acetyltobramycin,
1-desamino-1-oxo-3,6',3''-tri-N-acetylkanamycin A, the 5-epi, 5-epi-azido-5-deoxy, 5-epi-amino-5-deoxy analogs of the foregoing and of 1-desamino-1-oxo-3,2',6'-tri-N-(2,2,2-trichloroethoxycarbonyl)-3''-N-acetylgentamicin $C_{1a}$.

EXAMPLES

EXAMPLE 1

A. Sisomicin and 1-Epi-sisomicin

Dissolve 2.7 gms. of ammonium acetate in 100 ml. dry methanol. Adjust the pH of the solution to 5 using dry hydrogen chloride in methanol. Add 2 gm. of 1-desamino-1-oxo-3,2',6'-tri-N-acetyl sisomicin from Preparation 2A and stir the mixture at 25° C for 7 hours. Then add 1.8 gm. of sodium cyanoborohydride and stir the mixture for 18 hours at 25° C. Filter the mixture and evaporate the filtrate to dryness. Dissolve the resultant solid in 100 ml. of 5% aqueous sodium hydroxide and heat at reflux under an argon atmosphere for 50 hours. Cool the mixture and neutralize with Amberlite IRC 50 ($H^+$) resin. Wash the resin with 2 liters of water, then elute the resin with 2.5 liters of 7% ammonium hydroxide solution. Evaporate the basic eluates and chromatograph the residue on a silica gel column (160 × 5 cm) using chloroform-methanol-7% ammonium hydroxide (1:2:1) as the eluant. Evaporate the more polar eluates and rechromatograph the residue on a silica gel column (160 × 2.5 cm.) utilizing the lower phase of a chloroform-methanol-concentrated ammonium hydroxide solution (2:1:1) as the eluant. Follow the eluates by thin layer chromatography to obtain the products of the process in order of their increasing polarity.

(a) Evaporate the eluates containing the less polar sisomicin, dissolve the residue in water and pass over Amberlite IRA 401S ($OH^-$) resin, concentrate and lyophilize to obtain sisomicin: $[\alpha]_D^{26} + 188.9°$ ($H_2O$); $\delta$ ($D_2O$) 1.18 (3H, s, 4''—$CH_3$), 2.48 (3H, s, 3''—$NCH_3$), 4.83 (1H, m, $H_4'$), 5.04 (1H, d, $J_1''$, 2'' 4Hz, $H_1''$) and 5.30 ppm. (1H, d, $J_1'$, 2' 2Hz, $H_1'$); $\delta$ c ($D_2O$) 51.8 ($C_1$), 100.6 ($C_1'$) and 101.5 ppm ($C_1''$).

(b) Evaporate the eluates containing the more polar 1-epi-sisomicin, dissolve the residue in water and pass over Amberlite IRA 401S ($OH^-$) resin, concentrate and lyophilize to obtain 1-epi-sisomicin: $[\alpha]_D^{28} + 177.8°$ ($H_2O$); $\delta$ ($D_2O$) 1.29 (3H, s, 4''—$CH_3$), 2.61 (3H, s, 3''—$NCH_3$), 5.02 (1H, m, $H_4'$), 5.10 (1H, d, $J_1''$, $_2''$ 3.5 Hz, $H_1''$) and 5.46 ppm (1H, d, $J_1'$, $_2'$ 2Hz, $H_1'$); $\delta$ c ($D_2O$) 47.4 ($C_1$), 95.8 ($C_1''$) and 100.7 ppm ($C_1'$).

B. 4,6-Di-O-(aminoglycosyl)-1,3-diaminocyclitols and 1-epimers thereof

In a manner similar to that described in Example 1A by utilizing as starting compounds the products of Preparations 1A, 1B, 2B, 3A, 3B, 4A and 4B there are obtained, after removal of the N-blocking groups and selective chromatography, the corresponding 4,6-di-O-(aminoglycosyl)-1,3-diaminocyclitols and their 1-epimers.

The procedure for the removal of the N-blocking groups will be dependent on the type of blocking groups to be removed. For example, (a) when acetyl blocking groups are employed, the procedure is as in Example 1A, (b) when trifluoroacetyl blocking groups are employed, the procedure utilizes concentrated ammonium hydroxide at 25°–40° C for about 100 hours, (c) when trichloroethoxycarbonyl blocking groups are employed, the procedure utilizes Zn and 10% acetic acid in methanol at reflux for 3 hours, (d) when a combination of blocking groups are employed, e.g. trichloroethoxycarbonyl and acetyl groups, the procedure for removal is as in Example 1A.

EXAMPLE 2

A. 1-Epi-N-ethylsisomicin and 1-N-ethylsisomicin

Dissolve 1.62 gms. ethylamine in 100 ml. anhydrous methanol and adjust the solution to pH 5.5 by the addition of a solution of methanol saturated with anhydrous hydrogen chloride gas. To this solution add 4 gms of 1-desamino-1-oxo-3,2',6'-tri-N-acetylsisomicin from Preparation 2A and stir the reaction mixture at 25° C for about 7 hours. Then add 1.76 gm. sodium cyanoborohydride and stir the reaction mixture at 25° C for 18 hours.

During this time the pH will gradually rise from about pH 5 to about pH 6.9. Concentrate the solution in vacuo and take up the residue in 200 ml. 5% aqueous sodium hydroxide and heat the mixture at reflux for about 50 hours under an atmosphere of argon. Cool the mixture and neutralize with Amberlite IRC 50 ($H^+$) resin and wash the resin with 2 liters of water. Elute the resin with 2.5 liters of a 7% ammonium hydroxide solution. Evaporate the basic eluates and chromatograph the residue on a silica gel column (160 × 7 cm.) using the lower phase of a chloroform-methanol-14% ammonium hydroxide solution (2:1:1) as the eluant. Follow the eluates by thin layer chromatography to obtain the products of the procecess in order of their increasing polarity.

(a) Evaporate the eluates containing the less polar 1-epi-N-ethylsisomicin, dissolve the residue in water and pass over Amberlite IRA 401S ($OH^-$) resin, concentrate and lyophilize to obtain 1-epi-N-ethylsisomicin: $[\alpha]_D^{26}$ + 195.9° ($H_2O$); $\nu$ max (KBr) 3350, 1680, 1050, 1020 cm.$^{-1}$; $\delta$ ($D_2O$) 1.12 (3H, t, J 7.5 Hz, —NHCH$_2$CH$_3$), 1.27 (3H, s, 4″—CH$_3$), 2.57 (3H, s, 3″—NCH$_3$), 4.96 (1H, m, H$_4$′), 5.03 (1H, d, J$_1$″, $_2$″ 4Hz, H$_1$″) and 5.41 ppm (1H, d, J$_1$′, $_2$′ 2Hz, H$_1$′); $\delta$ c ($D_2O$) 52.7 (C$_1$), 95.8 (C$_1$″) and 100.9 ppm (C$_1$′).

(b) Evaporate the eluates containing the more polar, 1-N-ethylsisomicin, dissolve the residue in water and pass over Amberlite IRA 401S ($OH^-$) resin, concentrate and lyophilize to obtain 1-N-ethylsisomicin: $[\alpha]_D^{26}$ + 129.5° ($H_2O$); $\nu$ max (KBr) 3350, 1680, 1050, 1020 cm.$^{-1}$; $\delta$ ($D_2O$) 1.07 (3H, t,—NHCH$_2$CH$_3$), 1.21 (3H, s, 4″-CH$_3$), 2.53 (3H, s, 3″—NCH$_3$), 4.89 (1H, m, H$_4$′), 5.00 (1H, d, J$_1$″, $_2$″ 4Hz, H$_1$″) and 5.36 ppm. (1H, d, J$_1$′, $_2$′ 2Hz, H$_1$′); $\delta$ c ($D_2O$) 57.9 (C$_1$), 100.8 (C$_1$′) and 102.2 ppm. (C$_1$″).

B. 1-Epi-N-ethyl and 1-N-ethyl-4,6-di-O-(aminoglycosyl)-1,3-diaminocyclitols In a manner similar to that described in Example 2A, by utilizing as starting compounds the products of Preparations 1A, 1B, 2B, 3A, 3B, 4A and 4B there are obtained, after removal of the N-blocking groups as described in Example 1B and selective chromatography, the corresponding 1-epi-N-ethyl and 1-N-ethyl-4,6-di-O-(aminoglycosyl)-1,3-diaminocyclitols.

EXAMPLE 3

A. 1-Epi-N-methylgentamicin C$_1$ and 1-N-methylgentamicin C$_1$

Add 480 mg. methylamine to 23 ml. of dry methanol. Adjust the pH of the solution to 6 with the addition of a solution of methanol saturated with dry hydrogen chloride gas. To this add 1 gm. of 1-desamino-1-oxo-3,2′-di-N-trifluoroacetylgentamicin C$_1$ (sulphate salt). The pH was readjusted to 6 by addition of methylamine. Add 460 mg. of sodium cyanoborohydride and stir the reaction mixture at 25° C for 20 hours. Maintain the pH at 5.5 to 6. Add 20 ml. of concentrated ammonium hydroxide and keep the mixture at 25° C for 100 hours. Concentrate the solution to dryness and chromatograph the residue on a silica gel column (165 × 2.5 cm) using the lower phase of a chloroform-methanol-concentrated ammonium hydroxide solution (2:1:1) as the eluant. Follow the eluates by thin layer chromatography to obtain the products of the process in order of their increasing polarity. (a) Concentrate the less polar eluates containing 1-epi-N-methylgentamicin C$_1$. Rechromatograph the residue on a silica gel column (160 × 2.5 cm.) using chloroform-methanol-concentrated ammonium hydroxide (30:10:1) as the eluant, followed by the lower phase of a chloroform-methanol-concentrated ammonium hydroxide solution (2:1:1) as the eluant. Concentrate the eluates containing 1-epi-N-methylgentamicin C$_1$. Dissolve the residue in water and pass over Amberlite IRA 401S ($OH^-$) resin and lyophilize to obtain 1-epi-N-methylgentamicin C$_1$, $[\alpha]_D^{26}$ + 193.6° ($H_2O$); $\delta$ ($D_2O$) 0.99 (3H, d, J 6.5 Hz, 6′-CH$_3$), 1.13 (3H, s, 4″-CH$_3$), 2.25 (6H, s, 1-NCH$_3$ and 6′-NCH$_3$), 2.44 (3H, s, 3″-NCH$_3$), 4.93 (1H, d, J$_1$″, $_2$″ 4Hz, H$_1$″) and 5.07 ppm. (1H, d, J$_1$′, $_2$′ 3.5 Hz, H$_1$′); $\delta$ c ($D_2O$) 54.6 (C$_1$), 96.1 (C$_1$″) and 102.7 ppm. (C$_1$′).

(b) Concentrate the more polar fractions and rechromatograph on a silica gel column (110 × 1 cm.) using the lower phase of a chloroform-methanol-concentrated ammonium hydroxide solution (2:1:1) as the eluant. Monitor the eluates by thin layer chromatography and concentrate to a residue. Dissolve the residue in water and pass over Amberlite IRA 401S ($OH^-$) resin. Concentrate and lyophilize to obtain 1-N-methylgentamicin C$_1$, $[\alpha]_D^{26}$ + 122.4° ($H_2O$); $\delta$ ($D_2O$) 1.04 (3H, d, J 6.5 Hz, 6′,-CH$_3$), 1.18 (3H, s, 4″-CH$_3$), 2.29 (3H, s, 6′-NCH$_3$), 2.32 (3H, s, 1-NCH$_3$), 2.49 (3H, s, 3″-NCH$_3$), 4.95 (1H, d, J$_1$″, $_2$″ 4Hz, H$_1$″) and 5.13 ppm. (1H, d, J$_1$′, $_2$′ 3.5 Hz, H$_1$′); $\delta$ c ($D_2O$) 58.9 (C$_1$), 101.8 (C$_1$″) and 102. ppm. (C$_1$′).

B. 1-N-Methyl and 1-epi-N-methyl-4,6-di-O-(aminoglycosyl)-1,3-diaminocyclitols In a manner similar to that described in Example 3A, by utilizing as starting compounds the products of Preparations 1B, 2A, 2B, 3A, 3B, 4A and 4B there are obtained, after removal of the N-blocking groups as described in Example 1B, and selective chromatography the corresponding 1-N-methyl and 1-epi-N-methyl-4,6-di-O-(aminoglycosyl)-1,3-diaminocyclitols.

EXAMPLE 4

A. 1-Epi-N-iopropylgentamicin C$_1$ and 1-N-isopropylgentamicin C$_1$

Add 600 mg. of isopropylamine to 60 ml. of anhydrous methanol and adjust the pH of the solution to 6 by adding a solution of methanol saturated with dry hydrogen chloride gas. To this solution add 1 gm. of 1-desamino-1-oxo-3,2′-di-N-trifluoroacetylgentamicin C$_1$ (sulfate salt) and readjust the pH to 6 by the addition of isopropylamine. To the solution add 500 mg. of sodium cyanoborohydride and stir the reaction mixture at 25° C for 16 hours, maintaining the pH at 5.5–6. Then add 30 ml. of concentrated ammonium hydroxide and keep the mixture at about 25° C for 72 hours. Concentrate the solution to dryness and chromatograph the residue on a silica gel column (160 × 2.5 cm.) using the lower phase of a chloroform-methanol-concentrated ammonium hydroxide solution (2:1:1) as the eluant. Monitor the eluates by thin layer chromatography to obtain the products of the process in order of their increasing polarity.

(a) Evaporate the eluates containing the less polar 1-epi-N-isopropylgentamicin C$_1$, dissolve the residue in water and pass over Amberlite IRA 401S ($OH^-$) resin and lyophilize to obtain 1-epi-N-isopropylgentamicin C$_1$: $\delta$ ($D_2O$) 1.00 (3H, d, J 6.5 Hz, 6′-CH$_3$), 1.03 (3H, d, J 6.5 Hz, —CH (CH$_3$)$_2$), 1.06 (3H, d, J 6.5 Hz, —CH (CH$_3$)$_2$), 1.15 (3H, s, 4″-CH$_3$), 2.39 (3H, s, 6′-NCH$_3$), 2.47 (3H, s, 3″-NCH$_3$), 4.87 (1H, d, J$_1$″, $_2$″4Hz, H$_1$″) and 5.14 ppm. (1H, d, J$_1$′, $_2$′3.5 Hz, H$_1$′); δ c (D$_2$O) 50.5 (C$_1$), 95.7 (C$_1$″) and 102.5 ppm. (C$_1$′).

(b) Evaporate the eluates containing the more polar 1-N-isopropylgentamicin C$_1$, dissolve the residue in water and pass over Amberlite IRA 401S (OH$^-$) resin and lyophilize to obtain 1-N-isopropylgentamicin C$_1$, δ (D$_2$O) 1.00 (3H, d, J 6.5 Hz, 6′-CH$_3$), 1.02 (6H, d, J 6.5 Hz, —CH (CH$_3$)$_2$) 1.15 (3H, s, 4″-CH$_3$), 2.44 (3H, s, 6′-NCH$_3$), 2.49 (3H, s, 3″-NCH$_3$), 4.95 (1H, d, J$_1$″, $_2$″ 4Hz, H$_1$″) and 5.20 ppm. (1H, d, J$_1$′, $_2$′ 3.5 Hz, H$_1$′); δ c (D$_2$O) 54.5 (C$_1$), 102.2 (C$_1$″) and 102.2 ppm. (C$_1$′).

EXAMPLE 5

A. 1-epi-N-(β-hydroxyethyl)-gentamicin C$_1$ and 1-N-(β-hydroxyethyl)-gentamicin C$_1$ Dissolve 720 mg. of ethanolamine in 30 ml. of dry methanol, adjust the pH of the solution to 6 by addition of a solution of methanol saturated with dry hydrogen chloride gas. To the solution add 1.3 gm. of 1-desamino-1-oxo-3,2′-di-N-trifluoroacetylgentamicin C$_1$ (sulfate salt), and readjust the pH to about 6 with the addition of ethanolamine. Add 600 mg. of sodium cyanoborohydride and stir the reaction mixture at about 25° C for 17 hours maintaining the pH at 5.5-6. Add 10 ml. concentrated ammonium hydroxide and allow the mixture to remain at 25° C for about 48 hours. Concentrate the solution and chromatograph the residue on a silica gel column (160 × 2.5 cm.) using the lower phase of a chloroform-methanol-concentrated ammonium hydroxide solution (2:1:1) as the eluant. Monitor the eluate by thin layer chromatography to obtain the products of the process in order of their increasing polarity.

(a) Concentrate the less polar eluates containing 1-epi-N-(β-hydroxyethyl) gentamicin C$_1$. Rechromatograph the residue on a silica gel column (160 × 2 cm.) using chloroform-methanol-7% ammonium hydroxide solution (1:2:1) as the eluant. Concentrate the eluates containing 1-epi-N-(β-hydroxyethyl) gentamicin C$_1$, dissolve the residue in water and pass over Amberlite IRA 401S (OH$^-$) resin and lyophilize to obtain 1-epi-N-(β-hydroxyethyl) gentamicin C$_1$, [α]$_D^{26}$ + 154.3° (H$_2$O); δ (D$_2$O) 0.99 (3H, d, J 6.5 Hz, 6′-CH$_3$), 1.14 (3H, s, 4″-CH$_3$), 2.27 (3H, s, 6′-NCH$_3$), 2.45 (3H, s, 3″-NCH$_3$), 4.96 (1H, d, J$_1$″, $_2$″ 4Hz, H$_1$″) and 5.08 ppm. (1H, d, J$_1$′, $_2$′ 3.5 Hz, H$_1$′); δ c (D$_2$O) 52.4 (C$_1$), 96.0 (C$_1$″) and 102.2 ppm. (C$_1$′).

(b) Concentrate the more polar eluates containing 1-N-(β-hydroxyethyl) gentamicin C$_1$. Rechromatograph the residue on a silica gel column (160 × 2 cm.) using chloroform-methanol-7% ammonium hydroxide solution (1:2:1) as the eluant. Concentrate the eluates containing 1-N-(β-hydroxyethyl)-gentamicin C$_1$, dissolve the residue in water and pass over Amberlite IRA 401S (OH$^-$) resin and lyophilize to obtain 1-N-(β-hydroxyethyl)-gentamicin C$_1$, [α]$_D^{26}$ + 98.0° (H$_2$O), δ (D$_2$O) 0.99 (3H, d, J 6.5 Hz, 6′-CH$_3$), 1.13 (3H, s, 4″-CH$_3$), 2.28 (3H, s, 6′-NCH$_3$), 2.45 (3H, s, 3″-NCH$_3$), 4.97 (1H, d, J$_1$″, $_2$″ 4 Hz, H$_1$″) and 5.11 ppm. (1H, d, J$_1$′, $_2$′ 3.5 Hz, H$_1$′); δ c (D$_2$O) 57.3 (C$_1$), 101.5 (C$_1$″) and 102.6 ppm. (C$_1$′).

B. 1-epi-N-(β-hydroxyethyl) and 1-N-(β-hydroxyethyl)-4,6-di-O-(aminoglycosyl)-1,3-diaminocyclitols In a manner similar to that described in Example 5A, by utilizing as starting compounds the products of Preparations 1B, 2A, 2B, 3A, 3B, 4A and 4B there are obtained, after removal of the N-blocking groups as described in Example 1B and selective chromatography the corresponding 1-epi-N-(β-hydroxyethyl) and 1-N-(β-hydroxyethyl)-4,6-di-O-(aminoglycosyl)-1,3-diaminocyclitols.

EXAMPLE 6

A. 1-epi-N-(β-Phenylethyl)-gentamicin C$_1$ and 1-N-(β-Phenylethyl)gentamicin C$_1$ Dissolve 1.44 gm. of β-phenylethylamine in 30 ml. of dry methanol and adjust the pH of the solution to 6 by the addition of methanol saturated with dry hydrogen chloride gas. To this solution add 1.3 gm. of 1-desamino-1-oxo-3,2′-di-N-trifluoroacetylgentamicin C$_1$ (sulphate salt) and readjust the pH of the solution to 6 by means of 2-phenylethylamine. Add 600 mg. of sodium cyanoborohydride and stir the reaction mixture at 25° C for 19 hours, maintaining the pH at 5.5-6. Add 20 ml. of concentrated ammonium hydroxide to the reaction and allow the mixture to remain at 25° C for 116 hours. Concentrate the solution to dryness and chromatograph the residue on a silica gel column (160 × 2.5 cm.) using the lower phase of a chloroform-isopropanolconcentrated ammonium hydroxide solution (2:1:1) as the eluant. Follow the eluates by thin layer chromatography to obtain the product of the process in order of their increasing polarity.

(a) Evaporate the eluates containing the less polar 1-epi-N-(β-phenylethyl)-gentamicin C$_1$, dissolve the residue in water and pass over Amberlite IRA 401S (OH$^-$) resin and lyophilize to obtain 1-epi-N-(β-phenylethyl)-gentamicin C$_1$, [α]$_D^{26}$ + 152.1° (H$_2$O); δ (D$_2$O) 0.99 (3H, d, J 6.5 Hz, 6′-CH$_3$), 1.12 (3H, s, 4″-CH$_3$), 2.27 (3H, s, 6′-NCH$_3$), 2.44 (3H, s, 3″-NCH$_3$), 4.81 (1H, d, J$_1$″, $_2$″ 4 Hz, H$_1$″), 5.05 (1H, d, J$_1$′, $_2$′ 3.5 Hz, H$_1$′) and 7.24 ppm. (5H, s, —C$_6$H$_5$); δ c (D$_2$O) 52.4 (C$_1$), 96.0 (C$_1$″) and 102.6 ppm. (C$_1$′).

(b) Evaporate the eluates containing the more polar 1-N-(β-phenylethyl)-gentamicin C$_1$, dissolve the residue in water and pass over Amberlite IRA 401S (OH$^-$) resin and lyophilize to obtain 1-N-(β-phenylethyl)-gentamicin C$_1$, [α]$_D^{26}$ + 99.4° (H$_2$O): δ (D$_2$O) 0.99 (3H, d, J 6.5 Hz, 6′-CH$_3$), 1.10 (3H, s, 4″-CH$_3$), 2.28 (3H, s, 6′-NCH$_3$), 2.43 (3H, s, 3″-NCH$_3$), 4.88 (1H, d, J$_1$″, $_2$″ 4 Hz, H$_1$″), 5.08 (1H, d, J$_1$′, $_2$′ 3.5 Hz, H$_1$′) and 7.33 ppm. (5H, s, —C$_6$H$_5$); δ c (D$_2$O) 57.1 (C$_1$), 101.0 (C$_1$″) and 102.4 ppm. (C$_1$′).

B. 1-epi-N-(β-phenylethyl) and 1-N-(β-phenylethyl)-4,6-di-O-(aminoglycosyl)-1,3-diaminocyclitols In a manner similar to that described in Example 6A by utilizing as starting compounds the products of Preparations 1B, 2A, 2B, 3A, 3B, 4A and 4B there are obtained, after the removal of the N-blocking groups as described in Example 1B and selective chromatography, the corresponding 1-epi-N-(β-phenylethyl) and 1-N-(β-phenylethyl)-4,6-di-O-(aminoglycosyl)-1,3-diaminocyclitols.

EXAMPLE 7

A. 1-Epi-N-(γ-dimethylaminopropyl)-sisomicin and 1-N-(γ-dimethylaminopropyl)-sisomicin Dissolve 2.08 gm. of γ-dimethylaminopropylamine in 100 ml. of dry methanol and adjust the pH of the solution to 5.7 by the addition of methanol saturated with dry hydrogen chloride gas. To this solution add 2.13 gm. 1-desamino-1-oxo-3,2',6'-tri-N-acetylsisomicin and stir the reaction mixture at 25° C for 7 hours under dry argon. Then add 857 mg. of sodium cyanoborohydride and stir the reaction mixture at 25° C for 18 hours. Concentrate the solution and take up the residue in 100 ml. 5% aqueous sodium hydroxide and heat the mixture at reflux under an argon atmosphere for 50 hours. Cool the solution and neutralize with Amberlite IRC 50 (H$^+$) resin. Wash the resin with 1.5 liters of water and then elute with 2 liters of 7% ammonium hydroxide solution. Concentrate the basic eluates and chromatograph the residue on a silica gel column (160 × 5 cm.) using the lower phase of a chloroform-methanol-concentrated ammonium hydroxide solution (2:1:1) as the eluant. Rechromatograph these eluates on a silica gel column (160 × 3.5 cm.) using the same eluant. Monitor the eluates by thin layer chromatography to obtain the products of the process in order of their increasing polarity, (a) Evaporate the less polar eluates containing 1-epi-N-(γ-dimethylaminopropyl)-sisomicin. Dissolve the residue in water and pass over Amberlite IRA 401S (OH$^-$) resin and lyophilize to obtain 1-epi-N-(γ-dimethylaminopropyl)-sisomicin, $[\alpha]_D^{26} + 162.5°$ (H$_2$O); δ (D$_2$O) 1.21 (3H, s, 4"-CH$_3$), 2.19 (6H, s, —N (CH$_3$)$_2$), 2.52 (3H, s, 3"-NCH$_3$), 4.90 (1H, m, H$_4$'), 5.00 (1H, d, J$_1$", $_2$" 4 Hz, H$_1$") and 5.38 ppm. (1H, d, J$_1$', $_2$' 2 Hz, H$_1$'); δ c (D$_2$O) 52.7 (C$_1$), 95.9 (C$_1$") and 100. q ppm. (C$_1$').

(b) Evaporate the more polar eluates containing 1-N-(γ-dimethylaminopropyl)-sisomicin. Dissolve the residue in water and pass over Amberlite IRA 401S (OH$^-$) resin and lyophilize to obtain 1-N-(γ-dimethylamino-propyl)-sisomicin; $[\alpha]_D^{26} + 112.3°$ (H$_2$O); δ (D$_2$O) 1.20 (3H, s, 4"-CH$_3$), 2.19 (6H, s, —N (CH$_3$)$_2$), 2.50 (3H, s, 3"-NCH$_3$), 4.88 (1H, m, H$_4$'), 4.97 (1H, d, J$_1$", $_2$" 4 Hz, H$_1$") and 5.34 ppm. (1H, d, J$_1$', $_2$' 2 Hz, H$_1$'); δ c (D$_2$O) 57.9 (C$_1$), 100.8 (C$_1$') and 102.2 ppm. (C$_1$").

B. 1-Epi-N-(γ-dimethylaminopropyl) and 1-N-(γ-dimethylaminopropyl)-4,6-di-O-(aminoglycosyl)-1,3-diaminocyclitols In a manner similar to that described in Example 7A by utilizing as starting compounds the products of Preparations 1A, 1B, 2B, 3A, 3B, 4A and 4B there are obtained, after removal of the N-blocking groups as described in Example 1B and selective chromatography, the corresponding 1-epi-N-(γ-dimethylaminopropyl) and 1-N-(γ-dimethylaminopropyl)-4,6-di-O-(amino-glycosyl)-1,3-diaminocyclitols.

EXAMPLE 8

Acid Addition Salts

A. Sulfate Salts (Sulfuric Acid Addition Salts)

Dissolve 5 gm. of 1-epi-N-ethylsisomicin in 25 ml. of water and adjust the pH of the solution to 4.5 with 1N sulfuric acid. Pour into about 300 ml. of methanol with vigorous agitation, continue the agitation for about 10 - 20 minutes and filter. Wash the precipitate with methanol and dry at about 60° C in vacuo to obtain the corresponding 1-epi-N-ethylsisomicin sulfate.

In like manner, the sulfate salts of the compounds of Examples 1A, 1B, 2B, 3A, 3B, 4A, 4B, 5A, 5B, 6A, 6B, 7A and 7B may also be prepared.

B. Hydrochloride Salts

Dissolve 5 gm. of 1-epi-N-ethylsisomicin in 25 ml. of water. Acidify with 2N-hydrochloric acid to pH 5. Lyophilize to obtain the corresponding 1-epi-N-ethylsisomicin hydrochloride.

In like manner, the hydrochloride salts of the compounds of Examples 1A, 1B, 2B, 3A, 3B, 4A, 4B, 5A, 5B, 6A, 6B, 7A and 7B may also be prepared.

The present invention includes within its scope pharmaceutical compositions comprising our novel 1-epi-N-X-derivatives of 4,6-di-O-(aminoglycosyl)-1,3-diaminocyclitols with a compatible, pharmaceutically acceptable carrier, or coating. Also included within our invention is the method of eliciting an antibacterial response in a warm-blooded animal having a susceptible bacterial infection which comprises administering to said animal a nontoxic, antibacterially effective amount of a member selected from the group consisting of a 1-epi-N-X-derivative of a 4,6-di-O-(aminoglycosyl)-1,3-diaminocyclitol having antibacterial activity.

As discussed hereinabove, the 1-epi-N-X-derivatives of 4,6-di-O-(aminoglycosyl)-1,3-diaminocyclitols of this invention and the non-toxic pharmaceutically acceptable acid addition salts thereof are broad spectrum antibacterial agents which, advantageously, exhibit activity against organisms, particularly gram-negative organisms. Thus, the compounds of this invention can be used alone, or in combination with other antibiotic agents to prevent the growth, or reduce the number of bacteria in various environments. They may be used, for example, to disinfect laboratory glassware, dental and medical equipment contaminated with *Staphylococcus aureus*, or other bacteria. The activity of the 1-epi-N-X-4,6-di-O-(aminoglycosyl)-1,3-diaminocyclitols against gram-negative bacteria renders them useful for combating infections caused by gram-negative organisms, e. g. species of *E. coli*, and Pseudomonas. Our compounds, e. g. 1-epi-sisomicin and 1-epi-N-ethylisisomicin have veterinary applications, particularly in the treatment of mastitis in cattle and Salmonella induced diarrhea in domestic animals such as the dog and the cat.

In general, the dosage administered of the 1-epi-N-X-4,6-di-O-(aminoglycosyl)-1,3-diaminocyclitols will be dependent upon the age and weight of the animal species being treated, the mode of administration, and the type and severity of bacterial infection being prevented, or reduced.

The 1-epi-N-X-4,6-di-O-(aminoglycosyl)-1,3-diaminocyclitols and the pharmaceutically acceptable acid addition salts thereof may be administered orally. They may also be applied topically in the form of ointments, both hydrophilic and hydrophobic, in the form of lotions which may be aqueous, non-aqueous, or other emulsion type, or in the form of creams. Pharmaceutical carriers useful in the preparation of such formulations will include, for example, such substances as water, oils, fats, waxes, polyesters, polyols and the like.

In general, the topical preparations will contain from about 0.1 to about 3.0 gms. of the compounds of this invention per 100 gms. of ointment, creams or lotion. The topical preparations are usually applied gently to lesions from about 2 to about 5 times a day.

For oral administration the antibacterials of this invention may be compounded in the form of tablets, capsules, elixers, or the like, or may even be admixed with animal feed. It is in these dosage forms that the antibacterials are most effective for treating bacterial infections of the gastrointestinal tract which infections cause diarrhea.

The antibacterials of this invention may be utilized in liquid form such as solutions, suspensions and the like for otic and opthalmic use and may also be administered parenterally via intramuscular, intravenous, subcutaneous and intrasternal injection. The injectable solution, or suspension will usually be administered at from about 1 mg. of about 15 mgs. of antibacterial per kilogram of body weight per day divided into about 2 to about 4 doses. The precise dose depends on the stage and severity of the infection, the susceptibility of the infecting organism to the antibacterial and the individual characteristics of the animal species being treated.

The following formulations are to exemplify some of the dosage forms in which the antibacterial agents of this invention and their derivatives may be employed:

Formulation 1

| Tablet | 10 mg. Tab. | | 25 mg. Tab. | | 100 mg. Tab. | |
|---|---|---|---|---|---|---|
| 1-epi-sisomicin | 10.50 | * mg. | 26.25 | * mg. | 105.00 | * mg. |
| Lactose, impalpable powder | 197.50 | mg. | 171.25 | mg. | 126.00 | mg. |
| Corn starch | 25.00 | mg. | 25.00 | mg. | 35.00 | mg. |
| Polyvinyl-pyrrolidone | 7.50 | mg. | 7.50 | mg. | 7.50 | mg. |
| Magnesium Stearate | 2.50 | mg. | 2.50 | mg. | 3.50 | mg. |
| | 234.0 | mg. | 232.5 | mg. | 277.0 | mg. |

* 5% excess

Procedure

Prepare a slurry consisting of the 1-epi-sisomicin, lactose and polyvinylpyrrolidone. Spray dry and the slurry. Add corn starch and magnesium stearate. Mix and compress into tablets on a suitable press to the specified weight.

Formulation 2

| Ointment | |
|---|---|
| 1-epi-sisomicin | 1.0 gm. |
| Methyl paraben USP | 0.5 gm. |
| Propyl paraben USP | 0.1 gm. |
| Petrolatum | to 1000 gm. |

Procedure (1) Melt the petrolatum.

(2) Mix the 1-epi-sisomicin, methyl paraben and propyl paraben with about 10% of molten petrolatum and make a slurry. Mill the slurry and add to the balance of the petrolatum. Cool to room temperature with agitation.

We claim:

1. A 1-epi-N-X-4,6-di-O-(aminoglycosyl)-1,3-diaminocyclitol selected from the group consisting of 1-epi-N-X-gentamicin A, 1-epi-N-X-gentamicin B, 1-epi-N-X-gentamicin $B_1$, 1-epi-N-X-gentamicin $C_1$, 1-epi-N-X-gentamicin $C_{1a}$, 1-epi-N-X-gentamicin $C_2$, 1-epi-N-X-gentamicin $C_{2a}$, 1-epi-N-X-gentamicin $C_{2b}$, 1-epi-N-X-gentamicin $X_2$, 1-epi-N-X-kanamycin A, 1-epi-N-X-kanamycin B, 1-epi-N-X-3',4'-dideoxykanamycin B, 1-epi-N-X-sisomicin, 1-epi-N-X-verdamicin, 1-epi-N-X-tobramycin, 1-epi-N-X-Antibiotic G-52, 1-epi-N-X-Antibiotic G-418, 1-epi-N-X-Antibiotic 66-40B, 1-epi-N-X-Antibiotic 66-40D, 1-epi-N-X-Antibiotic JI-20A, 1-epi-N-X-Antibiotic JI-20B, the 5-epi, 5-epi-azido-5-deoxy, 5-epi-amino-5-deoxy analogs of the foregoing; and 1-epi-N-X-Antibiotic Mu-1, 1-epi-N-X-Antibiotic Mu-2, 1-epi-N-X-Antibiotic Mu-4, 1-epi-N-X-Antibiotic Mu-5;

and the pharmaceutically acceptable acid addition salts thereof, wherein X is a substituent selected from the group consisting of hydrogen, alkyl, alkenyl, cycloalkyl, cycloalkylalkyl, aralkyl, hydroxyalkyl, aminoalkyl, alkylaminoalkyl, dialkylaminoalkyl, aminohydroxyalkyl, alkylaminohydroxyalkyl and dialkylaminohydroxyalkyl, said X substituent having less than 9 carbon atoms with the proviso that, said aminohydroxyalkyl, alkylaminohydroxyalkyl and dialkylaminohydroxyalkyl substituents must have the amino and hydroxyl groups on different carbon atoms, and that neither substituent be on the carbon atom alpha to the 1-amino function.

2. A compound of claim 1 wherein said 6-aminoglycosyl is garosaminyl and said 1,3-diaminocyclitol is 2-deoxystreptamine.

3. A compound of claim 2 wherein said compound is 1-epi-N-X-4-O-(aminoglycosyl)-6-O-garosaminyl-2-deoxystreptamine, wherein X is hydrogen.

4. A compound of claim 2 wherein said compound is 1-epi-N-X-4-O-(aminoglycosyl)-6-O-garosaminyl-2-deoxystreptamine, wherein X has 2-4 carbon atoms.

5. A compound of claim 3 which is 1-epi-gentamicin $C_1$.

6. A compound of claim 3 which is 1-epi-gentamicin $C_{1a}$.

7. A compound of claim 3 which is 1-epi-sisomicin.

8. A compound of claim 3 which is 1-epi-verdamicin.

9. A compound of claim 4 which is 1-epi-N-ethylgentamicin $C_1$.

10. A compound of claim 4 which is 1-epi-N-($\beta$-hydroxyethyl) gentamicin $C_1$.

11. A compound of claim 4 which is 1-epi-N-propyl-gentamicin $C_1$.

12. A compound of claim 4 which is 1-epi-N-($\gamma$-aminopropyl) gentamicin $C_1$.

13. A compound of claim 4 which is 1-epi-N-($\delta$-aminobutyl) gentamicin $C_1$.

14. A compound of claim 4 which is 1-epi-N-ethyl-gentamicin $C_{1a}$.

15. A compound of claim 4 which is 1-epi-N-($\beta$-hydroxyethyl) gentamicin $C_{1a}$.

16. A compound of claim 4 which is 1-epi-N-propyl-gentamicin $C_{1a}$.

17. A compound of claim 4 which is 1-epi-N-($\gamma$-aminopropyl) gentamicin $C_{1a}$.

18. A compound of claim 4 which is 1-epi-N-($\delta$-aminobutyl) gentamicin $C_{1a}$.

19. A compound of claim 4 which is 1-epi-N-ethyl-sisomicin.

20. A compound of claim 4 which is 1-epi-N-($\beta$-hydroxyethyl) sisomicin.

21. A compound of claim 4 which is 1-epi-N-propyl-sisomicin.

22. A compound of claim 4 which is 1-epi-N-($\gamma$-aminopropyl) sisomicin.

23. A compound of claim 4 which is 1-epi-N-($\delta$-aminobutyl) sisomicin.

24. A compound of claim 4 which is 1epi-N-ethylverdamicin.

25. A compound of claim 4 which is 1-epi-N-($\beta$-hydroxyethyl) verdamicin.

26. A compound of claim 4 which is 1-epi-N-propyl-verdamicin.

27. A compound of claim 4 which is 1-epi-N-($\gamma$-aminopropyl) verdamicin.

28. A compound of claim 4 which is 1-epi-N-($\delta$-aminobutyl) verdamicin.

29. The method of eliciting an antibacterial response in a warm-blooded animal having a susceptible bacterial infection which comprises administering to said animal a non-toxic anti-bacterially effective amount of a 1-epi-N-X-4,6-di-O-(aminoglycosyl)-1,3-diaminocyclitol selected from the group consisting of 1-epi-N-X-gentamicin A, 1-epi-N-X-gentamicin B, 1-epi-N-X-gentamicin $B_1$, 1-epi-N-X-gentamicin $C_1$, 1-epi-N-X-gentamicin $C_{1a}$, 1-epi-N-X-gentamicin $C_2$, 1-epi-N-X-gentamicin $C_{2a}$, 1-epi-N-X-gentamicin $C_{2b}$, 1-epi-N-X-gentamicin $X_2$, 1-epi-N-X-kanamycin A, 1-epi-N-X-kanamycin B, 1-epi-N-X-3',4'-dideoxykanamycin B, 1-epi-N-X-sisomicin, 1-epi-N-X-verdamicin, 1-epi-N-X-tobramycin, 1-epi-N-X-Antibiotic G-52, 1-epi-N-X-Antibiotic G-418, 1-epi-N-X-Antibiotic 66-40B, 1-epi-N-X-Antibiotic 66-40D, 1-epi-N-X-Antibiotic JI-20A, 1-epi-N-X-Antibiotic JI-20B, the 5-epi, 5-epi-azido-5-deoxy, 5-epi-amino-5-deoxy analogs of the foregoing; 1-epi-N-X-Antibiotic Mu-1, 1-epi-N-X-Antibiotic Mu-2, 1-epi-N-X-Antibiotic Mu-4, 1-epi-N-X-Antibiotic Mu-5;

and the pharmaceutically acceptable acid addition salts thereof, wherein X is a substituent selected from the group consisting of hydrogen, alkyl, alkenyl, cycloalkyl, cycloalkylalkyl, aralkyl, hydroxyalkyl, aminoalkyl, alkylaminoalkyl, dialkylaminoalkyl, aminohydroxyalkyl, alkylaminohydroxyalkyl and dialkylaminohydroxyalkyl, said X substituent having less than 9 carbon atoms with the proviso that, said aminohydroxyalkyl, alkylaminohydroxyalkyl and dialkylaminohydroxyalkyl substituents must have the amino and hydroxyl groups on different carbon atoms, and that neither substituent be on the carbon atom alpha to the 1-amino function.

30. A pharmaceutical composition comprising an anti-bacterially effective amount of a 1-epi-N-X-4,6-di-O-(aminoglycosyl)-1,3-diaminocyclitol selected from the group consisting of: 1-epi-N-X-gentamicin A, 1-epi-N-X-gentamicin B, 1-epi-N-X-gentamicin $B_1$, 1-epi-N-X-gentamicin $C_1$, 1-epi-N-X-gentamicin $C_{1a}$, 1-epi-N-X-gentamicin $C_2$, 1-epi-N-X-gentamicin $C_{2a}$, 1-epi-N-X-gentamicin $C_{2b}$, 1-epi-N-X-gentamicin $X_2$, 1-epi-N-X-kanamycin A, 1-epi-N-X-kanamycin B, 1-epi-N-X-3',4'-dideoxykanamycin B, 1-epi-N-X-sisomicin, 1-epi-N-X-verdamicin, 1-epi-N-X-tobramycin, 1-epi-N-X-Antibiotic G-52, 1-epi-N-X-Antibiotic G-418, 1-epi-N-X-Antibiotic 66-40B, 1-epi-N-X-Antibiotic 66-40D, 1-epi-N-X-Antibiotic JI-20A, 1-epi-N-X-Antibiotic JI-20B, the 5-epi, 5-epi-azido-5-deoxy, 5-epi-amino-5-deoxy analogs of the foregoing; 1-epi-N-X-Antibiotic Mu-1, 1-epi-N-X-Antibiotic Mu-2, 1-epi-N-X-Antibiotic Mu-4, 1-epi-N-X-Antibiotic Mu-5, the pharmaceutically acceptable acid addition salts thereof, together with a non-toxic pharmaceutically acceptable carrier, wherein X is a substituent selected from the group consisting of hydrogen, alkyl, alkenyl, cycloalkyl, cycloalkylalkyl, aralkyl, hydroxyalkyl, aminoalkyl, alkylaminoalkyl, dialkylaminoalkyl, aminohydroxyalkyl, alkylaminohydroxyalkyl and dialkylaminohydroxyalkyl, said X substituent having less than 9 carbon atoms with the proviso that, said aminohydroxyalkyl, alkylaminohydroxyalkyl and dialkylaminohydroxyalkyl substituents must have the amino and hdyroxyl groups on different carbon atoms, and that neither substituent be on the carbon atom alpha to the I-amino function.

* * * * *